United States Patent [19]
Quon et al.

[11] Patent Number: 5,916,211
[45] Date of Patent: Jun. 29, 1999

[54] PERMANENT HAIR REMOVAL USING VISIBLE RED WAVELENGTH SPECTRUM LASERS

[76] Inventors: Hew W. Quon; David K. Quon, both of 805 Juarez St., Montebello, Calif. 90640; Wanda A. Quon, 808 N. Hill St., Los Angeles, Calif. 90012

[21] Appl. No.: 08/890,970

[22] Filed: Jul. 10, 1997

Related U.S. Application Data

[63] Continuation of application No. 08/552,790, Nov. 3, 1995, abandoned.

[51] Int. Cl.$^6$ ..................................................... A61N 5/06
[52] U.S. Cl. ..................................... 606/9; 606/3; 607/89
[58] Field of Search ................................ 606/2, 3, 9, 12, 606/131, 133; 607/88, 89

[56] References Cited

U.S. PATENT DOCUMENTS

| | | | |
|---|---|---|---|
| 4,388,924 | 6/1983 | Weissman et al. | 606/9 |
| 4,617,926 | 10/1986 | Sutton | 606/9 |
| 5,059,192 | 10/1991 | Zaias | 606/9 |
| 5,182,857 | 2/1993 | Simon | 606/9 |
| 5,226,907 | 7/1993 | Tankovich | 606/9 |
| 5,425,728 | 6/1995 | Tankovich | 606/9 |

*Primary Examiner*—Michael Peffley
*Attorney, Agent, or Firm*—Loeb & Loeb LLP; Michael J. Ram

[57] ABSTRACT

A device for permanently removing hair and a process for using that device comprising a laser emitting light in the visible red wave length spectrum, the laser light being used to destroy the hair follicle. A high energy laser is used with the light being delivered in pulses of from about 1 to 1000 microseconds.

2 Claims, No Drawings

PERMANENT HAIR REMOVAL USING VISIBLE RED WAVELENGTH SPECTRUM LASERS

This is a continuation of application Ser. No. 08/552,790, filed Nov. 3, 1995 now abandoned.

BACKGROUND

The present invention relates to a process for removing unwanted hair on humans or animals.

Hair grows in three different cycles. The traditional method of hair removal, namely thermolysis or electrolysis, require the use of a needle or a chemical. Further, these methods can only destroy hairs in their anagen stage. Still further, the chemicals can cause a reaction on the skin surface and the needle can cause injury to the skin as well as be a source for infection.

Thus, there is a need for a process for removing hair during all stages of hair development and without the use of harsh chemicals or instruments which can cause scarring or be a source of infection.

SUMMARY

These needs are met by the present invention which comprises a high power laser emitting a red wavelength beam of light with a sufficiently long pulse time to destroy the hair follicle. With a properly configured laser, the laser light selectively and permanently destroys the hair follicle without damaging the surrounding tissue or blood vessels.

DESCRIPTION

Hair grows in three different cycles. Thermolysis and electrolysis are only effective in the anagen stage. However, all hair follicles, regardless of the stage of development of the hair, share a basic property in that the hair follicle contains abundant melanin. I have now discovered that by use of a high powered laser emitting a beam of visible red light of an appropriate power density and pulsewidth, each individual hair can be selectively destroyed by coupling directly with the melanin within the hair follicle without causing injury to other tissue.

Permanent destruction of hair is accomplished by focusing the optical output of a high power laser (10–50 joules/$cm^2$) operating in the red wavelength spectrum (600–800 nm) on the base of the hair to be eliminated. The laser generated light is able to penetrate the skin or transmit along the pore out of which the hair is growing to reach the melanin in the hair follicle. One skilled in the art will recognize that the laser beam is not delivered continuously but consists of a series of pulses of light. If the duration of individual pulses of the laser beam is from 1 to 1000 microseconds the laser energy will destroy the hair follicle without causing damage to the surrounding vascular tissue or skin, thus resulting in permanent destruction of the hair.

Although the present invention has been described in detail with reference to a certain preferred version and use thereof, other versions and uses are possible. For example, the process described can be supplemented and improved by use of other techniques described in prior art. However, such added procedures, or other procedures to prepare the skin surface for treatment, only enhance the process described above. Therefore, the spirit and scope of the appended claims should not be limited to the description of the preferred versions contained herein.

What is claimed is:

1. A method for permanently removing hair comprising:
   a) generating a pulsed beam of red spectrum laser light using a laser having a power output from 10 joules/$cm^2$ to 50 joules/$cm^2$, and
   b) irradiating a hair follicle with the pulsed beam of light, said beam of light having a pulse duration of from 1 microsecond to 1000 microseconds.

2. The method of claim 1 wherein the beam of light has a wave length of from about 600 to about 800 nm.

* * * * *